United States Patent [19]
Heller et al.

[11] Patent Number: 5,628,755
[45] Date of Patent: May 13, 1997

[54] BALLOON CATHETER AND STENT DELIVERY SYSTEM

[75] Inventors: Mathias Heller, Winterthur, Switzerland; Alfonso M. Fernandez-Aceytuno, E-Las Palmas de Gran Canaria, Spain; Rainer Amann, Riedern am Sand, Germany; Roland Hirt, Schaffhausen; Jakob Willi, Hori, both of Switzerland

[73] Assignee: Schneider (Europe) A.G., Bulach, Switzerland

[21] Appl. No.: 547,186

[22] Filed: Oct. 24, 1995

[30] Foreign Application Priority Data

Feb. 20, 1995 [ES] Spain ........................... 9500456
Apr. 24, 1995 [EP] European Pat. Off. ........... 95106125

[51] Int. Cl.⁶ ........................................... A61F 11/00
[52] U.S. Cl. ........................... 606/108; 606/194; 604/96
[58] Field of Search ........................... 606/191, 192, 606/194, 197, 198, 108; 604/96, 282, 271, 280

[56] References Cited

U.S. PATENT DOCUMENTS

| | | | |
|---|---|---|---|
| 4,824,435 | 4/1989 | Giesy et al. | 604/49 |
| 5,171,305 | 12/1992 | Schickling et al. | 604/282 |
| 5,201,757 | 4/1993 | Heyn et al. | 606/198 |
| 5,242,399 | 9/1993 | Lau et al. | 604/104 |
| 5,246,421 | 9/1993 | Saab | 604/96 |
| 5,312,356 | 5/1994 | Engelson et al. | 604/282 |

FOREIGN PATENT DOCUMENTS

| | | |
|---|---|---|
| 0335341A1 | 10/1989 | European Pat. Off. |
| 0408245A1 | 1/1991 | European Pat. Off. |
| 0466518A2 | 1/1992 | European Pat. Off. |
| 0678307A2 | 10/1995 | European Pat. Off. |
| 9508965 | 4/1995 | WIPO |
| 96/19256 | 6/1996 | WIPO |

OTHER PUBLICATIONS

Spanish Utility Model Application No. 9401050 filed Apr. 19, 1994, and laid open Sep. 16, 1994, together with a certified English translation thereof.

Spanish Utility Model Application No. 9500456 filed Feb. 20, 1995, and laid open Jul. 16, 1995, the priority of which is claimed, together with a certified English Translation thereof.

European Patent Application Serial No. 94118900.3, filed Nov. 30, 1994, together with transmittal sheets.

United States Patent Application, Serial No. 08/548,786, filed Oct. 26, 1995, which is commonly owned by the assignee of this application.

*Primary Examiner*—Michael Buiz
*Assistant Examiner*—Kevin Truong
*Attorney, Agent, or Firm*—Peter C. Richardson; Lawrence C. Akers; Philip C. Strassburger

[57] ABSTRACT

The balloon catheter comprises a shaft with an elongated dilatation balloon mounted in the vicinity of the distal end thereof. Armature for preventing expansion of balloon segments are mounted on shaft proximally of the balloon and include an armature enclosed in a sleeve moveable over a proximal portion of the balloon.

14 Claims, 3 Drawing Sheets

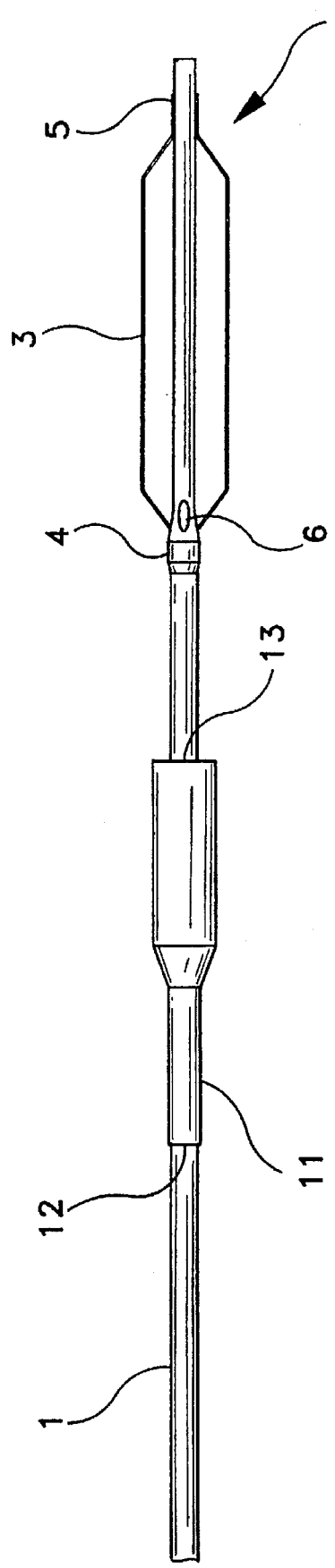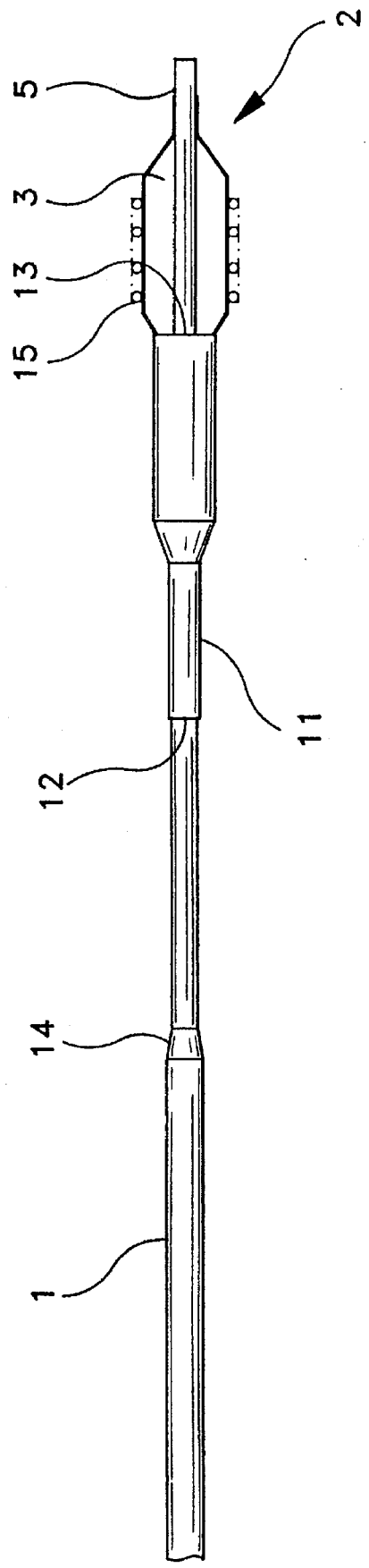

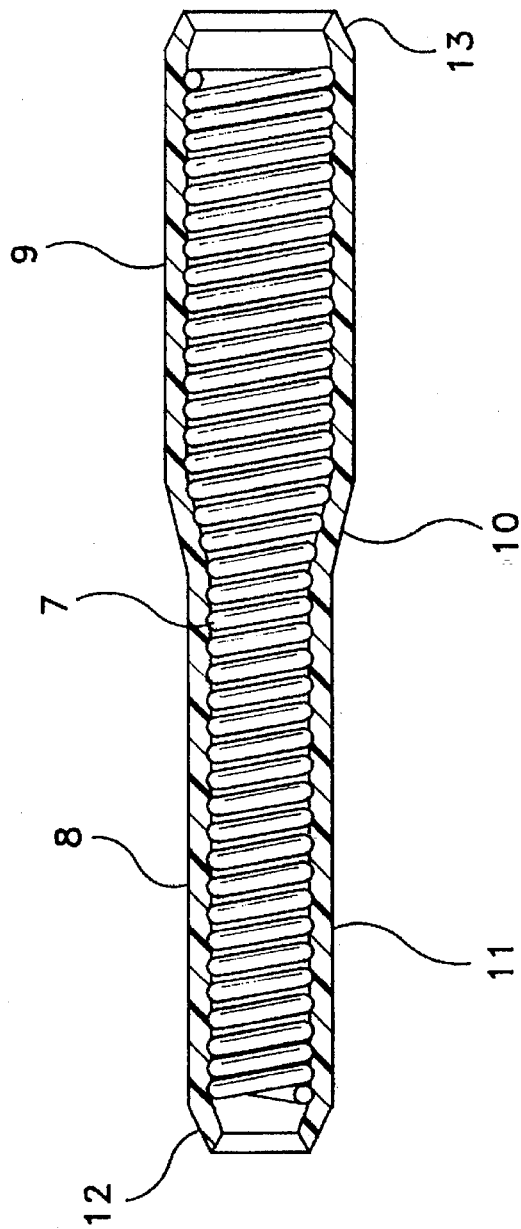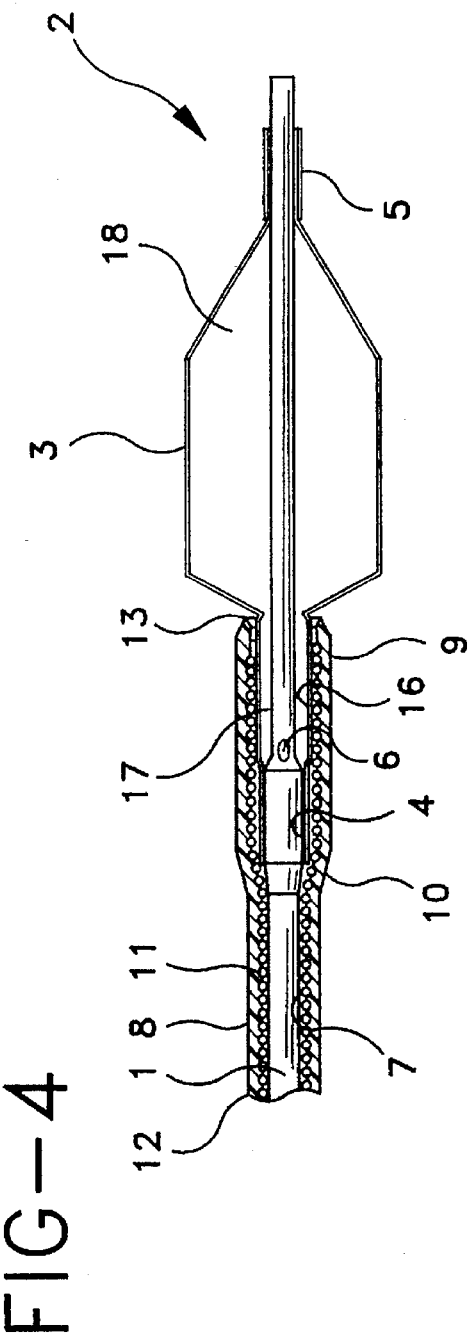

BALLOON CATHETER AND STENT DELIVERY SYSTEM

FIELD OF THE INVENTION

This invention relates to a balloon catheter comprising a tubular shaft having a proximal end and a distal end, an elongated dilatation balloon with proximal and distal ends, said balloon being mounted on said tubular shaft in the vicinity of the distal end thereof, and means secured on the tubular shaft for preventing expansion of balloon segments.

The invention also relates to a stent delivery system for a balloon expandable stent, comprising a balloon catheter with a tubular shaft having a proximal end and a distal end, and an elongated dilatation balloon with proximal and distal ends, said balloon being mounted on said tubular shaft in the vicinity of the distal end thereof.

BACKGROUND OF THE INVENTION

Balloon catheter technology makes use of balloons of fixed lengths, whereby the great number of medical procedures requiring balloon catheter technology makes it necessary to rely on several catheters of different balloon length. When a procedure requires, for example, two differently sized balloons, it is necessary to change balloon catheters or to act sequentially with the one length balloon available. Changing balloon catheter is costly while sequential action with the available balloon length may be a time-consuming and potentially hazardous procedure which may lead to injury of the patient or insufficient dilatations.

The balloon catheter is also an instrument of common use as a mechanism for transporting and applying a balloon expandable prosthesis, called a stent, for maintaining the patency of a vessel. The length of the balloon must be chosen as a function of the length of the stent, to avoid inappropriate expansion of the stent or damage to the vessel. This may also lead to the costly need of a plurality of balloon catheters to correctly and safety apply the stents.

U.S. Pat. No. 5,246,421 refers to a method of treating obstructed regions of bodily passages which provides for use of balloon catheters with adjustable length balloons. Accordingly, this document teaches the use of a balloon catheter in which an adjustable sheath is externally manipulated to partially surround and contain the dilatation balloon segment of the catheter in situ during a treatment procedure. By external manipulations sliding the sheath forwardly and backwardly to expose a predetermined length of the balloon segment prior to inflating the balloon, various balloon lengths can be obtained. The catheter body can comprise an elongated tube and a balloon attached by both its neck portions to two axially spaced locations on the elongated tube; the catheter can also have a catheter body defining a lumen with a balloon terminating such a body as an integral one piece assembly having a closed end. The document outlines that the described technology can be modified or tuned to be compatible with virtually any catheter constructions, including over the wire catheters and fixed wire catheters. In order to avoid creep of the sheath during or after inflation of the balloon tending to encover more balloon than originally selected, the position of the sheath may be firmly fixed, for example by a clamping device, prior to inflation of the balloon. The mere fact that the sheath is externally manipulated creates a substantial complication in the catheter construction, and the risk of having the sheath clogged up. In addition, the system is relatively cumbersome and rigid due to the multiplicity of elements resulting from the externally manipulated sheath over the catheter shaft, which may cause some difficulties for the treatment of tortuous or narrow vessels. And there may also be a friction problem between the sheath and catheter shaft which may add difficulties to the external manipulation of the sheath. There is no suggestion in this document that the moving sheath and resulting variable length balloon catheter could be envisaged as a system for matching the balloon length requirements for stent delivery.

European Patent Application No. 94118900.3 filed Nov. 30, 1994 by an applicant of the present invention shows a balloon catheter as described hereinbefore in which the tubular shaft comprises a guidewire lumen with an entry for the guidewire distal of the balloon and an exit for the guidewire distal of the proximal end of the tubular shaft, and means for preventing expansion of balloon segments comprising a not distensible sleeve attached to the tubular shaft either distal of the exit for the guidewire if said exit is proximal of the balloon or proximal of the exit for the guidewire if said exit is distal of the balloon. This document also shows a stent delivery system for a balloon expandable stent comprising a balloon catheter having the features as described hereabove. This development is specifically directed to modification of the length of the balloon in balloon catheters and stent delivery systems which make use of the fast and efficient technology known under the name MONORAIL®.

All documents cited herein, including the foregoing, are incorporated herein in their entireties for all purposes.

It is an object of this invention to further improve over the prior at by proposing a balloon catheter which is highly versatile and efficient, simple to manufacture, and easy and safe to use. A further object of the invention is to propose a stent delivery system which is also versatile and efficient, which is simple to manufacture, and which is easy and safe to operate. To this effect, the invention complies with the definitions given in the claims.

SUMMARY OF THE INVENTION

Accordingly, either for primary use of the balloon catheter, i.e. for dilatation of stenoses, or for stent delivery of a balloon expandable stent, it is very simple and easy to modify the length of the balloon while relying on a structure which remains absolutely safe, assuring full radial stability of the balloon catheter whatever the pressure of the balloon in the reduced configuration, and with the sleeve means enclosing the armature means providing a smooth atraumatic surface. There is no external manipulation of the balloon reduction arrangement during introduction, withdrawal or use of the balloon catheter, either for stenosis dilatation or for stent delivery within the patient's vessels. The construction of the catheter remains simple, without friction generating motion of elements along the vessel.

In practice, either for usage of the balloon catheter for dilatation of stenosed or for stent delivery, the balloon catheter may be devised for standard over the wire configuration, or for the technology known under the name MONORAIL®.

For stenosis dilatation purposes, the doctor may select at will the configuration of the balloon, full or reduced length, as he may proceed to a first dilatation with the full length balloon, and then withdraw the balloon catheter as usual along the guidewire, modify the operational length of the balloon by moving the armature and sleeve over the proximal portion of the balloon, and then insert the balloon catheter over the guidewire to rapidly reach the stenosis which has to be treated with a reduced balloon length. For stent delivery purposes, the doctor may effect the stenosis dilatation with the full length balloon and then withdraw the balloon catheter along the guidewire, reduce the operational length of the balloon by moving the armature and sleeve over the proximal portion of the balloon, install the stent in collapsed condition on the free distal segment of the balloon, and then reinsert the stent equipped balloon catheter over the guidewire to reach the required location in the vessel and expand the stent by balloon inflation.

Where the balloon catheter or stent delivery system comprises means for locking the armature means and sleeve means on the shaft either in a position proximal of the balloon or in a position over the proximal portion of the balloon, a safe arrangement is assured to avoid any risk of having the balloon modifying structure moving in an unwanted position either during insertion through the vessel or during withdrawal thereof.

Where the sleeve means have a constricted proximal end, coupling of the sleeve means and armature means enclosed thereby may be simply achieved over the shaft in the inoperative condition of the balloon reducing configuration. A smooth transition is also achieved between proximal end of the sleeve and the shaft.

Where the sleeve means have a constricted distal end, coupling of the sleeve means and armature means enclosed thereby over the balloon is achieved in operative condition of the balloon reducing structure, In addition, there is a smooth transition between sleeve and shaft or balloon. And furthermore, inflation of the balloon causes the proximal end of the balloon to lock within the armature and sleeve proximally of the constricted distal end of the sleeve, thereby achieving an automatical question free self-locking against any possibility of the armature and sleeve getting loose of the balloon in the proximal direction during the always delicate inflation procedure.

The shaft may comprise an enlarged portion proximal of the balloon to provide a locking friction seat for the armature means in the operative condition of the balloon reducing structure. And to take advantage of the existing structures, this enlarged portion may be formed at the proximal end of the balloon, preferably being made by a proximal fixture of the balloon on the shaft.

Where the shaft comprises a shoulder portion proximally of the armature and sleeve means, a further question free self-locking is achieved in the inoperative condition of the balloon reducing configuration, this shoulder portion providing a geometrical seat for the proximal structure of the sleeve marts, which geometrical seat may even provide an interpenetration fit with the proximal end of the armature means.

The armature means may have a distal portion having a first diameter and a proximal portion having a second diameter, in order to assure a low profile to the means for preventing expansion of balloon segments. Where this second diameter is smaller than the first diameter, lowest profile is achieved while assuring guidance for the expansion preventing structure and also providing room for the question free self-locking conditions as outlined hereinbefore. Within this configuration, the armature means may have an inner shoulder portion formed by a junction of the second diameter portion to the first diameter portion, thereby taking advantage of the two diameter configuration to provide a question free positioning for the expansion preventing means in the operative condition. And for ease of manufacture, the sleeve means may be made of two tubular elements connected to one another.

The armature means may be made of coiled materials or they may be made of braided material, both conditions assuring a good flexibility for travel along tortuous vessels as well as high radial resistance to balloon inflating pressure. When the armature means are made of a high density metal, the resulting radiopacity facilitates visualisation of the balloon reducing structure for balloon portioning purposes.

It is an advantage when the sleeve means have an inner configuration matching the configuration of the armature means, because an excellent transmission of forces is assured between armature means and sleeve means for safe handling and positioning of the sleeve and armature enclosed therein.

In summary, the present invention relates to a balloon catheter or a stent delivery system with a tubular shaft having a proximal end and a distal end, and an elongated dilatation balloon with proximal and distal ends. The balloon is mounted on the tubular shaft in the vicinity of the distal end thereof. Means secured on the tubular shaft prevents expansion of balloon segments, and has armature means surrounding the shaft proximally of the balloon for longitudinal motion over a proximal portion of the balloon, and sleeve means enclosing the armature means. The device may also have means for locking the armature means and sleeve means on the shaft either in a position proximal of the balloon or in a position over the proximal portion of the balloon. The sleeve means may have a constricted proximal end, and/or may have a constricted distal end. The shaft may have an enlarged portion proximal of the balloon, which may be formed at the proximal end of the balloon. The enlarged portion may be a proximal fixture of the balloon on the shaft. The shaft may have a shoulder portion proximally of the armature and sleeve means. The armature means have a distal portion having a first diameter and a proximal portion having a second diameter. The second diameter may be smaller than the first diameter. The armature means may have an inner shoulder portion formed by a junction of the second diameter portion to the first diameter portion. The sleeve means may be made of two tubular elements connected to one another, and may have a truncated core shape. The armature means may be made of coiled material or braided material. The armature means may be made of a high density metal. The sleeve means may have an inner configuration matching the configuration of the armature means.

These and other objects, features and advantages of the invention will become readily apparent from the following detailed description with reference to the accompanying drawings which show, diagrammatically and by way of example only, one embodiment of the invention.

DESCRIPTION OF THE DRAWINGS

FIG. 1 is a side elevation of a balloon catheter embodying the invention.

FIG. 2 is a side elevation of the balloon catheter of FIG. 1 in another condition.

FIG. 3 is an enlarged longitudinal section of a detail of FIG. 1.

FIG. 4 is an enlarged longitudinal section of a detail of FIG. 2.

DESCRIPTION OF PREFERRED EMBEDMENT

Figure 5:
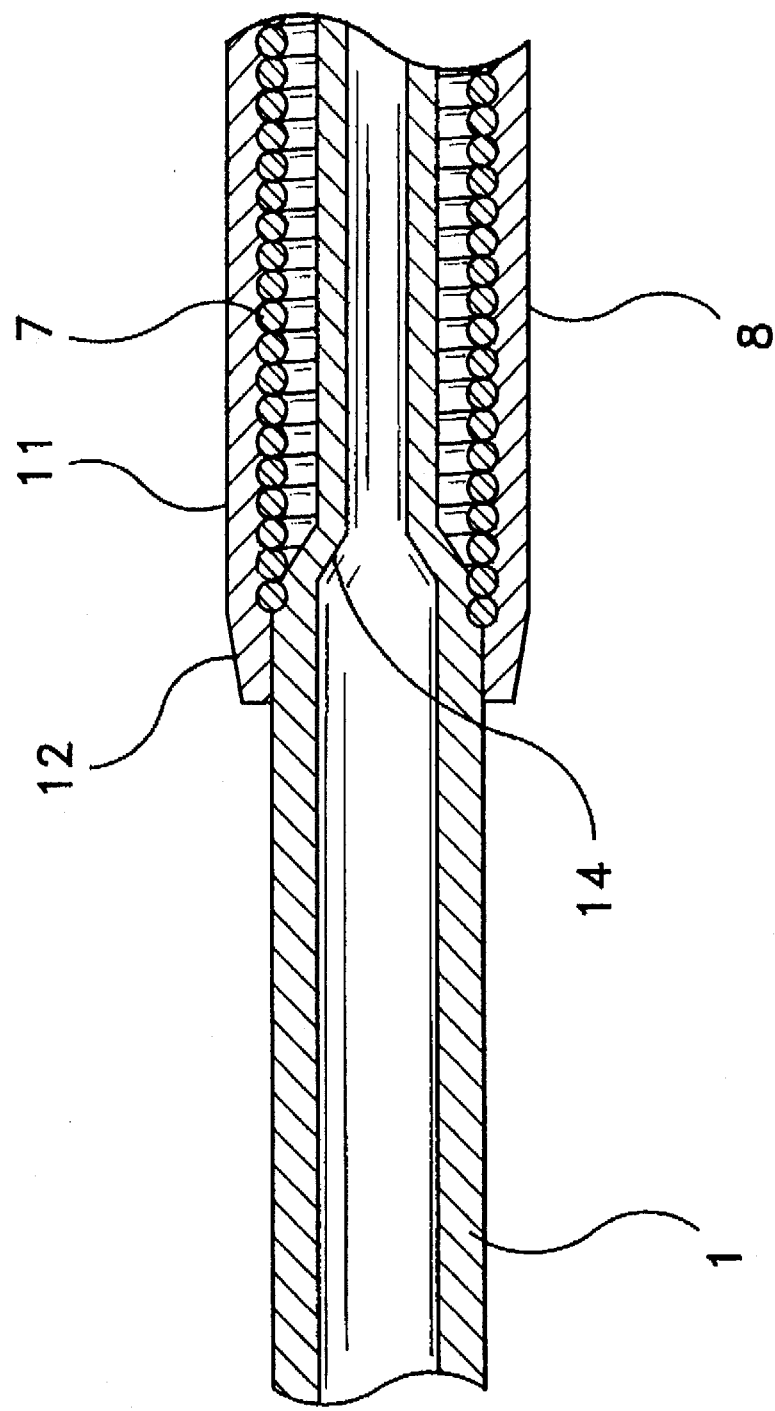
FIG. 5 is an enlarged longitudinal section of an another detail of FIG. 2.

The balloon catheter shown in FIG. 1 comprises a tubular shaft 1 having a proximal end (not shown) and a distal end 2. An elongated dilatation balloon 3 (shown in inflated condition) with proximal end 4 and distal end 5 is mounted on the shaft 1, in the vicinity of its distal end 2. As usual in the art, the balloon 3 has its distal end 5 and its proximal end 4 welded on the shaft 1, and such weldings constitute enlarged portions on the shaft, proximally and distally of the balloon. An aperture 6 in the shaft connects the interior of the balloon 3 to a fluid supplying lumen (not shown) extending within the shaft 1.

Means for preventing expansion of balloon segments are mounted on the tubular shaft 1, proximally of the balloon 3. These means for preventing expansion of balloon segments comprise an armature 7 (as clearly visible on FIG. 3) formed by a coiled metal wire, preferably a high density metal such as Tungsten, and a sleeve 11, preferably made of a substantially flexible polymer, enclosing said armature 7.

The armature 7 comprises a proximal portion 8, substantially cylindrical, and a distal portion 9, also substantially cylindrical. Portion 8 has a diameter which is smaller than the diameter of portion 9, and both portions are connected to one another by a junction forming a shoulder 10 inside the armature 7.

The armature 7 is embedded in sleeve 11 the inner configuration of which matches the configuration of the coiled armature, whereby a close interconnection is achieved between the two parts.

Sleeve 11 has a general configuration following that of armature 7. It has a constricted proximal end 12 and a constricted distal end 13.

Proximally of the armature 7 and sleeve 11, the shaft 1 has a shoulder 14. In the example shown, this shoulder 14 is due to an enlargement of the shaft section which so extends up to the proximal end (not shown) of the shaft. This is however not compulsory and the shaft may just have a constant diameter and a shoulder at the location shown for shoulder 14.

Operation of the balloon catheter is as follows.

When the balloon is to be used full length, or as a basic delivery position, the assembly of armature 7 and sleeve 11 is pushed proximally until the constricted proximal end 12 makes way onto shoulder 14 of shaft 1, as shown in FIG. 1. For extra safety, the sleeve may be pushed proximally until the material of shaft 1, thereby assuring an interpenetration fit, as shown in FIG. 5. In that condition, the balloon catheter may be safely inserted into the patient's vessel and withdrawn thereof without any risk of having the assembly of armature and sleeve moving on the catheter shaft.

For operation of the balloon in reduced size (Cf. FIGS. 2 and 4), it suffices to push (by hand) the sleeve 11 towards the proximal end of the balloon and to follow up that motion up to having the shoulder 10 of armature 7 abutting against the enlarged portion formed by the proximal fixture 4 of the balloon 3. At that time, the distal portion 9 of armature 7 partly engages and friction fits onto the enlargement provided for by the proximal welding 4 of the balloon 3 on the shaft 1.

Simultaneously, the distal end of armature 7 and sleeve 11 extend over a proximal portion of the balloon 3, thereby defining a neutralised length 16 for the balloon and providing a room 17 (FIG. 4) for part expansion of the balloon. Upon inflation of the balloon, the free portion 18 thereof expands normally while the neutralised portion 16 enclosed in room 17 expands for a dilatation limited to the contact between balloon 3 and armature 7. At that time, the constricted distal end of sleeve 11 is boxed between the two portions 16 and 18 of the balloon, thereby assuring automatic self locking of the sleeve and armature on the balloon. In that condition, the armature also guards against any unwanted dilatation of the sleeve 11. After expansion of the balloon as required, the balloon is deflated and the catheter may be withdrawn as usual, the armature 7 and sleeve 11 remaining in their position by friction fit and abutment on the balloon proximal fixture.

The balloon catheter shown may also be used as a stent delivery system for a balloon expandable stent 15 as shown in phantom on FIG. 2.

Variants may be envisaged without departing from the scope of the invention.

For instance, the coiled armature 7 could be replaced by a braided armature, preferably also made of a high density metal wire. And another structure can be devised for sleeve, for example truncated cone shape.

We claim:

1. A balloon catheter comprising a tubular shaft having a proximal end and a distal end; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon, the armature means adapted for longitudinal motion over a proximal portion of the balloon; sleeve means enclosing the armature means; and means for locking the armature and sleeve means on the shaft in a position either proximal of the balloon or over the proximal portion of the balloon.

2. The balloon catheter of claim 1 further comprising means for deploying a stent at a treatment site.

3. A balloon catheter comprising a tubular shaft having a proximal end and a distal end; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon, the armature means adapted for longitudinal motion over a proximal portion of the balloon; and sleeve means having a constricted proximal end and enclosing the armature means.

4. The balloon catheter of claim 3 further comprising means for deploying a stent at a treatment site.

5. A balloon catheter comprising a tubular shaft having a proximal end and a distal end; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon, the armature means adapted for longitudinal motion over a proximal portion of the balloon; and sleeve means having a constricted distal end and enclosing the armature means.

6. The balloon catheter of claim 5 further comprising means for deploying a stent at a treatment site.

7. A balloon catheter comprising a tubular shaft having a proximal end, a distal end, and a shoulder portion; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon, the armature means adapted for longitudinal motion over a proximal portion of the balloon; and sleeve means enclosing the armature means; wherein the shaft shoulder portion is disposed proximally of the armature and sleeve means.

8. The balloon catheter of claim 7 further comprising means for deploying a stent at a treatment site.

9. A balloon catheter comprising a tubular shaft having a proximal end and a distal end; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon the armature means adapted for longitudinal motion over a proximal portion of the balloon and having a distal portion having a first diameter and a proximal portion having a second diameter which is less than the first diameter; and sleeve means enclosing the armature means.

10. The balloon catheter of claim 9 further comprising means for deploying a stent at a treatment site.

11. A balloon catheter according to claim 9 wherein the armature means has an inner shoulder portion formed by a junction of the proximal portion and the distal portion.

12. A balloon catheter comprising a tubular shaft having a proximal end and a distal end; an elongated dilatation balloon with proximal and distal ends, the balloon being mounted on the tubular shaft in the vicinity of the distal end thereof; means secured on the tubular shaft for preventing expansion of balloon segments, the means for preventing expansion of balloon segments comprising armature means surrounding the shaft proximally of the balloon, the armature means adapted for longitudinal motion over a proximal portion of the balloon; and sleeve means enclosing the armature means and comprising two tubular elements connected to one another.

13. The balloon catheter of claim 12 further comprising means for deploying a stent at a treatment site.

14. A balloon catheter according to claim 13 wherein the sleeve means has a truncated conical shape.

* * * * *